United States Patent [19]
Rault et al.

[11] Patent Number: 5,599,812
[45] Date of Patent: Feb. 4, 1997

[54] TRICYCLIC PYRROLOPYRAZINE 5-HT$_3$-ACTIVE COMPOUNDS

[75] Inventors: Sylvain Rault, Moult; Jean-Charles Lancelot, Le Bourg; Hervé Prunier, Caen; Max Robba, Paris; Philippe Delagrange, Issy Les Moulineaux; Pierre Renard, Versailles; Gérard Adam, Le Mesnil Le Roi, all of France

[73] Assignee: Adir Et Compagnie, Courbevoie, France

[21] Appl. No.: 235,426

[22] Filed: Apr. 29, 1994

[30] Foreign Application Priority Data

Apr. 30, 1993 [FR] France .................. 93 05109

[51] Int. Cl.$^6$ ............ C07D 417/14; C07D 413/14; A61K 31/54; A61K 31/535
[52] U.S. Cl. ............ 544/238.2; 514/233.2; 514/250; 514/267; 544/60; 544/115; 544/251; 544/344; 544/346
[58] Field of Search .................. 544/251, 344, 544/346, 60, 115; 514/267, 250, 233.2, 228.2

[56] References Cited

PUBLICATIONS

Journal of Medicinal Chemistry 33, Washington US, pp. 2087–2093, 1990 Macor et al.
Chemical Abstracts 77, No. 19, 1972, columbus, Ohio, US; 126567y.
Campiani et al., Chemical Abstracts, 1991, 115:207,948d.

*Primary Examiner*—Mukund J. Shah
*Assistant Examiner*—Matthew V. Grumbling
*Attorney, Agent, or Firm*—The Firm of Gordon W. Hueschen

[57] ABSTRACT

The present invention relates to a compound selected from these of formula (I):

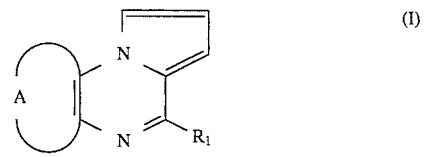

in which A and $R_1$ are as defined in the description, and medicinal product containing the same which is useful for treating a disorder linked to the 5-HT$_3$ receptors.

15 Claims, No Drawings

TRICYCLIC PYRROLOPYRAZINE 5-HT$_3$-ACTIVE COMPOUNDS

The present invention relates to new pyrrolopyrazine compounds, to processes for their preparation and to the pharmaceutical compositions which contain them.

The Applicant has now discovered new pyrrolopyrazine compounds which show a very high affinity for 5-HT$_3$ receptors which are selective with respect to other serotoninergic receptors.

The therapeutic potential and interest of pharmacological agents which act on 5-HT$_3$ receptors has been mentioned many times, especially in the review "5-HT$_3$ Receptors" (Kilpatrick G. J., Medicinal Research Reviews, 1990, 10 (4), pp 441–475).

Pyrroloquinoxalines are known in the literature (Campiani G. et al., Synthetic Communications, 1991, 21 (15–16), pp 1567–1576, Nagarajan K. et al., Indian J. Chem., 1972, 10, pp 344–350). Among these pyrroloquinoxalines, 4-(4-methylpiperazinyl)-7-(trifluoromethyl)pyrrolo[1,2-a]quinoxaline is especially known and is described exclusively as an agonist of 5-HT$_{1B}$ serotoninergic receptors (Neale R. F. et al., Eur. J. of Pharmacology, 1987, 136, pp 1–9 and Macor J. E. et al., J. Med. Chem., 1990, 33, pp 2087–2093).

More particularly, the present invention relates to the compounds of formula (I):

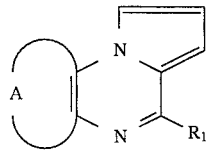

in which:

R$^1$ represents a group of formula:

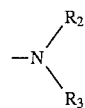

in which R$_2$ and R$_3$ form, with the nitrogen atom which carries them, a group chosen from:

piperazine, substituted piperazine, piperidine, substituted piperidine, pyrrolidine, substituted pyrrolidine, morpholine, morpholine substituted by one or a number of alkyl radicals, tetrahydropyridine, thiomorpholine, 5- to 12-membered azaspiro compound, 5 to 12-membered azaspiro compound substituted by one or a number of alkyl radicals or oxo groups, 7- to 12-membered mono- or bicyclic azacycloalkyl optionally including, in its skeleton, from 1 to 2 additional heteroatoms chosen from oxygen, sulfur and nitrogen, 7- to 12-membered mono- or bicyclic azacycloalkyl substituted by one or a number of alkyl radicals or oxo groups, optionally including, in its skeleton, from 1 to 2 additional heteroatoms chosen from oxygen, sulfur and nitrogen, a group —NH—(CH$_2$)$_k$—NH$_2$ in which k represents an integer equal to 2, 3 or 4, and a substituted group —NH—(CH$_2$)$_k$—NH$_2$ in which k is as defined above, and A forms, with the 2 carbon atoms to which it is bonded, a ring chosen from benzo, pyrido, pyrazino and pyrimidino; A being unsubstituted or substituted by one or a number of radicals chosen from:

alkyl, hydroxyl, alkoxy, acyl, alkoxycarbonyl, halogen, trifluoromethyl,

—(CH$_2$)$_m$-phenyl and —O—(CH$_2$)m-phenyl in which the phenyl ring is itself unsubstituted or substituted by one or a number of radicals chosen from halogen, alkyl, alkoxy, hydroxyl and trifluoromethyl; and m represents 0 or an integer from 1 to 4, —(CH$_2$)$_m$-piperazine in which the piperazine group is itself substituted or unsubstituted and m is as defined above, it being understood that if A forms, with the 2 carbon atoms to which it is bonded, a benzo ring which is unsubstituted or substituted by a trifluoromethyl or a fluorine, then R$_2$ and R$_3$ cannot form, with the nitrogen atom which carries them, a piperazine which is unsubstituted or substituted in the 4-position by a methyl or (methyl)phenyl radical, and that if A forms, with the 2 carbon atoms to which it is bonded, an unsubstituted benzo ring, then R$_2$ and R$_3$ cannot form, with the nitrogen atom which carries them, a morpholine or a dimethylaminopropylamino group, it being understood that the term "substituted" affecting the above piperazine, piperidine, pyrrolidine and —NH—(CH$_2$)$_k$—NH$_2$ groups means that these groups can be substituted by one or a number of halogen atoms, hydroxyl radicals, oxo radicals, R$_4$ radicals or radicals

with R$_4$ being chosen from:

alkyl, alkoxy, alkenyl which is unsubstituted or substituted by a phenyl radical which is itself unsubstituted or substituted by one or a number of radicals chosen from halogen, alkyl, alkoxy, hydroxyl and trifluoromethyl,

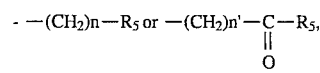

where n represents an integer from 1 to 5, n' represents an integer from 1 to 5, and where R$_5$ represents a radical chosen from phenyl, benzhydryl, thienyl, pyrrolyl, pyrrolidinyl, furyl, pyrimidinyl, pyridyl, methylenedioxyphenyl, ethylenedioxyphenyl, naphthyl, quinolyl, isoquinolyl, cycloalkyl and dicycloalkylmethyl; the term "cycloalkyl" representing a 3- to 12-membered mono- or bicyclic group, it being possible for these R5 radicals themselves to be substituted by one or a number of radicals chosen from halogen, trifluoromethyl, carboxyl, hydroxyl, alkyl or alkoxy, and $(CH_2)_{n'}$—$R_6$ where n' is as defined above and $R_6$ represents a group chosen from carboxyl, alkoxycarbonyl, amino, alkylamino, dialkylamino, —$SO_2NR_7R_8$ and —$CONR_7R_8$ in which $R_7$ and $R_8$ represent, each independently of the other, a hydrogen atom or an alkyl, to their optical isomers, and to their addition salts with a pharmaceutically acceptable acid or base, it being understood that, except when otherwise specified, the terms "alkyl", "alkoxy" and "acyl" represent linear or branched groups having from 1 to 6 carbon atoms, and the term "alkenyl" represents a linear or branched unsaturated group having from 2 to 6 carbon atoms.

Mention may be made, among pharmaceutically acceptable acids which can be used to form an addition salt with the compounds of the invention, by way of examples and without implied limitation, of hydrochloric, sulfuric, phosphoric, tartaric, malic, maleic, fumaric, oxalic, methanesulfonic, ethanesulfonic, camphoric and citric acids.

Mention may be made, among pharmaceutically acceptable bases which can be used to salify the compounds used according to the invention, by way of examples and without implied limitation, of sodium hydroxide, potassium hydroxide, triethylamine, diethylamine, ethanolamine, arginine, lysine and diethanolamine.

The invention relates to, for example:

the compounds of formula (I) in which A forms a benzo ring with the 2 carbon atoms to which it is bonded, the compounds of formula (I) in which A forms a pyrido ring with the 2 carbon atoms to which it is bonded, and the compounds of formula (I) in which $R_2$ and $R_3$ form, with the nitrogen atom which carries them, a piperazine which is substituted in the 4-position by a benzyl radical which is itself unsubstituted or substituted, their optical isomers, and their addition salts with a pharmaceutically acceptable acid or base.

The present invention applies to the process for the preparation of the compounds of formula (I), wherein:

either a compound of formula (II),

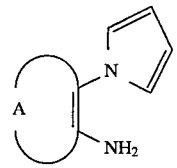

(II)

in which A is as defined in the formula (I), is brought to reflux in the presence of phosgene or a compound of formula (II/1),

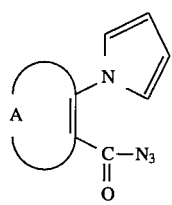

(II/1)

in which A is as defined in the formula (I), is heated in the presence or in the absence of solvent to obtain a compound of formula (I/a):

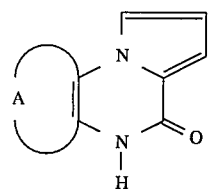

(I/a)

in which A is as defined above, which compound of formula (I/a) is subjected to a halogenating agent to obtain a compound of formula (I/b):

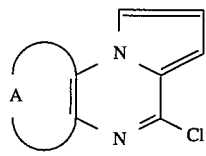

(I/b)

in which A is as defined above, which is then reacted with an amine of formula (III):

(III)

in which $R_2$ and $R_3$ are as defined in the formula (I), to obtain a compound of formula (I):

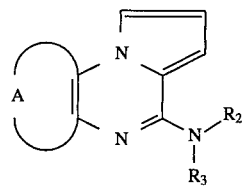

(I)

in which A, $R_2$ and $R_3$ are as defined above, it being possible for the compounds of formula (I) to be:

purified according to one or a number of purification methods chosen from crystallization, chromatography on a silica column, extraction, filtration and passing through charcoal and/or resin, separated, if appropriate, in the pure form or in the mixed form, into their possible optical isomers, and/or salified with a pharmaceutically acceptable acid or base.

The invention also applies to the process for the preparation of the compounds of formula (I), wherein:

a compound of formula (II'):

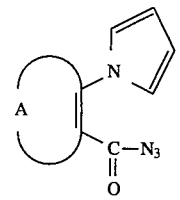

(II')

in which A is as defined in the formula (I), is reacted with an amine of formula (III):

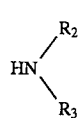

(III)

in which $R_2$ and $R_3$ are as defined in the formula (I), to obtain a compound of formula (V):

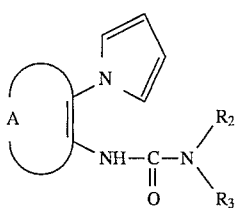

in which A, R$_2$ and R$_3$ are as defined above, which is then cyclized under the action of a halogenating agent and subjected to an alkaline treatment to give a compound of formula (I):

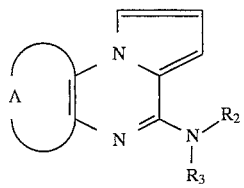

in which A, R$_2$ and R$_3$ are as defined above, it being possible for the compounds of formula (I) to be:

- purified according to one or a number of purification methods chosen from crystallization, chromatography on a silica column, extraction, filtration and passing through charcoal and/or resin,
- separated, if appropriate, in the pure form or in the mixed form, into their possible optical isomers,
- and/or salified with a pharmaceutically acceptable acid or base.

It is also possible to gain access to the compounds of formula (I) in which the substituent of A, with A as defined in the formula (I), and the group R1, with R$_1$ as defined in the formula (I), are identical by simultaneous grafting of the substituent of A and of R$_1$.

The starting materials used in the processes described above are:

- either commercially available,
- or easily accessible to those skilled in the art according to processes described in the literature.

The compounds of formula (I) have very advantageous pharmacological properties.

The Applicant has discovered that the compounds of the invention selectively had a high affinity for 5-HT$_3$ serotoninergic receptors.

Additionally, their powerful affinity for 5-HT$_3$ receptors was demonstrated both in vitro (measurement of the accumulation of $^{14}$-C-guanidinium in NG 108-5 cells, Example B of the present application) and in vivo (measurement of the Bezold-Jarisch reflex, Example C of the present application).

The compounds of the invention are thus capable of being used in the prevention and treatment of anxiety, depression, stress, psychoses, schizophrenia, disorders of the central nervous system, migraine, memory disorders, food behavioral disorders, alcoholism or pain and in the prevention and treatment of vomiting and stomach dumping disorders.

The invention also applies to the pharmaceutical compositions containing, as active principle, at least one of the compounds of formula (I) or one of its addition salts with a pharmaceutically acceptable acid or base in combination with one or a number of pharmaceutically acceptable excipients or vehicles.

Mention can be made, among the compositions according to the invention, by way of examples and without implied limitation, of those which are suitable for oral, parenteral, ocular, per- or transcutaneous, nasal, rectal, perlingual or respiratory administration and especially injectable preparations, aerosols, eye or nose drops, tablets, sublingual tablets, capsules, including gelatin capsules, lozenges, glossettes, suppositories, creams, ointments and gels.

The preparations thus obtained are generally provided in the dosed form and can contain, depending on the ailments treated, the age and the sex of the patient, from 0.01 to 100 mg of active principle to be taken from one to three times per day, preferably from 0.01 to 5 mg of active principle, particularly from 0.1 to 5 mg, for example 1 mg.

The examples which follow illustrate the invention and do not limit it in any way.

EXAMPLE 1:
4-(4-BENZYLPIPERAZINO)PYRROLO[1,2-a]-QUINOXALINE

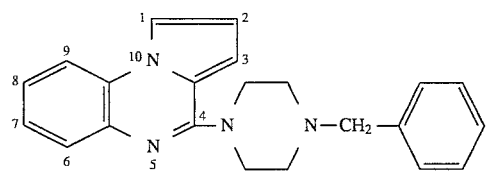

EXAMPLE 1

Stage A:
4,5-dihydro-4-oxopyrrolo[1,2-a]quinoxaline

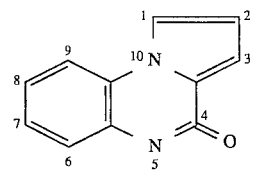

15 g (0.095 mol) of 2-(1-pyrrolyl)aniline is brought to reflux for 1 h 30 min, in 200 cm$^3$ of toluene, in the presence of 50 cm$^3$ of a 20% solution of phosgene in toluene. After cooling, the precipitate formed is filtered off, washed with ethyl ether, dried and recrystallized from acetonitrile (white powder sublimed at 270° C.).

Yield: 80%

Spectral characteristics:

Infrared ν cm$^{-1}$ (KBr): 1640 (C=O), main bands at 1360, 1080, 725 and 640.

NMR Spectrum (d$_6$-DMSO): δSH pyrrole protons: 8.13, 7.00, 6.63; δH C$_6$H$_4$: 7.96, 7.23.

Stage A': 2nd process 14.69 cm$^3$ (d=0.73) of triethylamine are added dropwise at 0° C. to a solution of 20 g (0.106 mol) of 2-(1-pyrrolyl)benzoic acid in a mixture (50/50) of acetone and acetonitrile. After stirring for 30 min, 10.13 cm$^3$ (d=1.135) of ethyl chloroformate are added dropwise so that the temperature remains between 0° and +5° C. and then, after stirring for 30 min, 6.89 g (0.106 mol) of sodium azide in solution in 30 cm$^3$ of water are added dropwise. The reaction mixture is stirred at 0° C. for 2 h and then poured into 600 cm$^3$ of water. The solution is extracted with 150 cm$^3$ of ether and the organic phase is separated by settling, dried and evaporated under reduced pressure. The azide formed is spontaneously and dangerously converted to 4,5-dihydro-4oxopyrrolo[1,2-a]quinoxaline by rearrangement. Sublimation at 270° C.

Stage B: 4-chloropyrrolo[1,2-a]quinoxaline

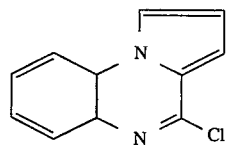

10 g (0.0543 mol) of 4,5-dihydro-4-oxopyrrolo[1,2-a] quinoxaline are brought to reflux in 180 cm$^3$ of phosphorus oxychloride and 10 cm$^3$ of pyridine for 5 h. After having been taken to dryness, the residue is taken up in 300 cm$^3$ of water, stirred and then neutralized with an aqueous ammonia solution. The precipitate is filtered off, washed with water, dried and recrystallized from ethyl acetate.

Melting point: 172° C.

Yield: 63%

Spectral characteristics:
Infrared ν cm−1 (KBr): main bands at: 1600, 1410, 750 and 720. NMR Spectrum (d$_6$-DMSO): δH pyrrole protons: 8.53, 7.00; δH$_6$, H$_7$, H$_8$, H9: 8.26, 7.80, 7.50.

Stage C:
4-(4-benzylpiperazino)pyrrolo[1,2-a]quinoxaline

A mixture of 2 g (0.0098 mol) of 4-chloropyrrolo[1,2-a] quinoxaline, 1.72 g of 1-benzylpiperazine and 1.04 g (0.0098 mol) of sodium carbonate is brought to 140° C. for 2 h 30 min in 30 cm$^3$ of dimethylformamide. After cooling, the solution is poured into 100 cm$^3$ of water with stirring and is then extracted with 150 cm$^3$ of ethyl ether. The ether phase is washed with 100 cm$^3$ of water, separated by settling, dried and then concentrated under reduced pressure. The dark-yellow residual oil is dissolved in 30 cm$^3$ of isopropyl alcohol and then 3 cm$^3$ of concentrated hydrochloric acid are added. After stirring for 30 min, the precipitate is filtered off and washed with 10 cm$^3$ of isopropyl alcohol and then with 20 cm$^3$ of anhydrous ethyl ether. Recrystallization solvent: acetonitrile (white powder).

Melting point (trihydrochloride): 182° C.

Yield: 51%

Spectral characteristics:
Infrared: ν cm$^{-1}$(KBr) 2550, 2650, 2880 NH$^+$, main bands at: 1500, 1580, 1410, 940 and 680.
NMR Spectrum (d$_6$-DMSO): δH C$_6$H$_5$F: 8.17, 7.63; δH pyrrole protons: 8.61, 7.45 and 6.98; δH CH$_2$: 4.67, 4.43, 3.43; δNH$^+$4.70.

EXAMPLE 2:
4-[4-(4-FLUOROBENZYL)PIPERAZINO]PYRROLE [1,2-a]QUNIOXALINE

The title compound is obtained by carrying out the reaction as in Example 1 but replacing 1-benzylpiperazine in Stage C with 1-(4-fluorobenzyl)piperazine. Recrystallization solvent: acetonitrile (white powder). Melting point (trihydrochloride): 182° C.

Yield: 49%

Spectral characteristics:
Infrared: ν cm$^{-1}$ (KBr) 2560, 2660, 2880 NH$^+$, main bands at: 1580, 1420, 1220 and 745
NMR Spectrum (d$_6$-DMSO): δH pyrrole protons: 8.60, 7.36 and 7.00; δH C$_6$H$_4$-F: 7.73 and 7.36, δH C$_6$H$_4$F: 8.20 and 7.36, δH CH$_2$: 4.46, 3.43; δH NH$^+$: 4.46

EXAMPLE 3 TO 10:

The compounds of the following examples are obtained by carrying out the reaction as in Examples 1 or 2 but using appropriately substituted 2-(1-pyrrolyl)aniline in Stage A and 1-benzylpiperazine or 1-(4-fluorobenzyl)piperazine in Stage C:

EXAMPLE 3: 4-(4-BENZYLPIPERAZINO)-7-CHLOROPYRROLO[1,2-a]QUINOXALINE

Stage A:
7-chloro-4,5-dihydro-4-oxopyrrolo[1,2-a]quinoxaline

Recrystallization solvent: acetonitrile

Melting point: >270° C.

Yield: 76%

Stage B: 4,7-dichloropyrrolo[1,2-a]quinoxaline

Recrystallization solvent: acetonitrile

Melting point: 204° C.

Yield: 59%

Stage C: 4-(4-benzylpiperazino)-7-chloropyrrolo[1,2-a]quinoxaline

Recrystallization solvent: acetonitrile

Melting point (trihydrochloride): 168° C.

Yield: 46%

Infrared: ν cm$^{-1}$ (KBr) 2600, 2700 NH$^+$, main bands at: 1600, 1510, 960 and 760.

NMR Spectrum (d$_6$-DMSO): δH pyrrole protons: 8.53, 7.33, 6.93; δH$_6$ H$_8$, H9:8.13, 7.60; δH C$_6$H$_5$: 7.33; C$_6$H$_5$: 7.33, δH NH$^+$4.83, δH CH$_2$: 4.43, 4.06, 3.36.

EXAMPLE 4:
7-CHLORO-4-[4-(4-FLUOROBENZYL)PIPERAZINO]PYRROLO[1,2-a]QUINOXALINE

Recrystallization solvent: acetonitrile

Melting point (trihydrochloride): 212° C.

Yield: 49%

Spectral characteristics:
Infrared: ν cm$^{-1}$ (KBr) 2620, 2720 (NH+), main bands at: 1600, 1515, 1230, 810 and 770.

NMR Spectrum (d$_6$-DMSO): δSH pyrrole protons: 8.56, 7.33, 6.93; δH$_6$, H$_8$, H9; 8.13, 7.33; δH C$_6$H$_4$-F: 7.76, 7.33; δH NH$^+$: 5.00; δH CH$_2$: 4.40, 4.00, 3.33.

EXAMPLE 5:
4-(4-BENZYLPIPERAZINO]-8-CHLOROPYRROLO [1,2-a]QUINOXALINE

Stage A:
8-chloro-4,5-dihydro-4-oxopyrrolo[1,2-a]quinoxaline

Recrystallization solvent: acetonitrile

Melting point: >270° C.

Yield: 64%

Stage B: 4,8-dichloropyrrolo[1,2-a]quinoxaline

Recrystallization solvent: acetonitrile

Melting point: 188° C.

Yield: 57%

Stage C: 4-(4-benzylpiperazino)-8-chloropyrrolo[1,2-a]quinoxaline

Recrystallization solvent: acetonitrile
Melting point (trihydrochloride): >210° C.
Yield: 37%
Spectral characteristics:
Infrared: ν cm$^{-1}$ (KBr) 2600, 2700 (NH$^+$), main bands at: 1595, 1430, 1390, 1120, 750 and 705.
NMR Spectrum (d$_6$-DMSO): δH pyrrole protons: 8.53, 6.93; δH$_6$, H$_7$, H9: 8.26, 8.10, 7.66; δH C$_6$H$_5$: 7.36; δH NH$^+$: 4.80; δH CH$_2$: 4.40, 4.03, 3.36.

EXAMPLE 6:
8-CHLORO-4-[4-(4-FLUOROBENZYL)PIPERAZINO]PYRROLO[1,2-a]QUINOXALINE

EXAMPLE 7:
4-[4-(4-FLUOROBENZYL)PIPERAZINO]-7-METHYLPYRROLO[1,2-a]QUINOXALINE

Stage A:
4,5-dihydro-7-methyl-4-oxopyrrolo[1,2-a]quinoxaline

Recrystallization solvent: acetonitrile
Sublimation at 240° C.
Yield: 40%

Stage B:
4-chloro-7-methylpyrrolo[1,2-a]quinoxaline

Recrystallization solvent: ethyl acetate
Melting point: 158° C.
Yield: 53%

Stage C:
4-[4-(4-fluorobenzyl)piperazino]-7-methylpyrrolo[1,2-a]quinoxaline

Recrystallization solvent: acetonitrile
Melting point (trihydrochloride): 206° C.
Spectral characteristics:
Infrared: ν cm$^{-1}$ (KBr) 2340, 2540, 2600 NH$^+$, main bands at: 1605, 1520, 1240, 960 and 770.
NMR Spectrum (d$_6$-DMSO): δH pyrrole protons: 8.55, 7.20, 7.00; δH$_6$, H$_8$, H9: 8.13, 7.96, 7.33; δH C$_6$H$_4$-F: 7.73, 7.33; δH NH$^+$: 4.66; δH CH$_2$: 4.40, 4.10, 3.40; δH CH$_2$:2.40

EXAMPLE 8:
4-(4-BENZYLPIPERAZINO)-7-METHYLPYRROLO[1,2-a]QUINOXALINE

EXAMPLE 9:
4-[4-(4-FLUOROBENZYL)PIPERAZINO]-7-METHOXYPYRROLO[1,2-a]QUINOXALINE

Stage A:
4,5-dihydro-7-methoxy-4-oxopyrrolo[1,2-a]quinoxaline

Recrystallization solvent: acetonitrile
Sublimation at 250° C.

Stage B:
4-chloro-7-methoxypyrrolo[1,2-a]quinoxaline

Recrystallization solvent: ethyl acetate
Melting point: 132° C.
Yield: 34%

Stage C: 4-[4-(4-fluorobenzyl)piperazino]-7-methoxypyrrolo[1,2-a]quinoxaline

Recrystallization solvent: acetonitrile
Melting point: 220° C.
Spectral characteristics:
Infrared: ν cm$^{-1}$ (KBr) 2600, 2700 NH$^+$, main bands at: 1600, 1510, 1235, 810 and 770.
NMR Spectrum (d$_6$-DMSO): δH pyrrole protons: 8.56, 7.20, 6.96; δH$_6$, H$_8$, H$_9$: 8.10, 7.90, 7.30; δH C$_6$H$_4$-F: 7.76, 7.30; δH NH$^+$: 4.80; δH CH$_2$: 4.40, 4.00, 3.33; δH OCH$_2$:3.82

EXAMPLE 10:
4-(4-BENZYLPIPERAZINO)-7-METHOXYPYRROLO-[1,2-a]QUINOXALINE

EXAMPLE 11:
6-(4-BENZYLPIPERAZINO)PYRIDO[3,2-e]-PYRROLO[1,2-a]PYRAZINE

The title compound is obtained by carrying out the reaction as in Example 1 but replacing 2-(1pyrrolyl)aniline in Stage A with 3-amino-2-(1-pyrrolyl)pyridine.

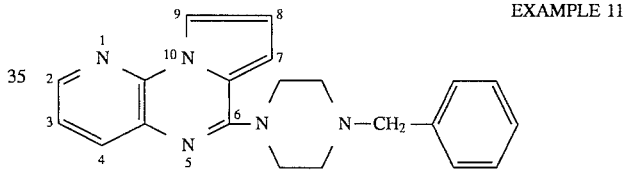

EXAMPLE 11

Stage A:
5,6-dihydro-6-oxopyrido[3,2-e]pyrrolo[1,2-a]pyrazine

Melting point: >265° C.
Reference: Lancelot et al., Chem. Pharm. Bull., 1985, Vol. 33, p. 2798.

Stage B:
6-chloropyrido[3,2-e]pyrrolo[1,2-a]pyrazine

Recrystallization solvent: acetonitrile
Melting point: 146° C.
Yield: 82%
Spectral characteristics:
Infrared: ν cm$^{-1}$ (KBr): main bands at: 1590, 1400, 1260, 1090, 790 and 730.
NMR Spectrum (d$_6$-DMSO): δH pyrrole protons: 8.33, 7.03, 6.93; δH$_2$, H$_3$, H$_4$ (pyridine protons): 8.50, 8.13 and 7.50.

Stage C: 6-(4-benzylpiperazino)pyrido[3,2-e]pyrrolo[1,2-a]pyrazine

Recrystallization solvent: acetonitrile
Melting point (trihydrochloride): 186° C.
Yield: 81%
Spectral characteristics:

Infrared: ν cm⁻¹ (KBr) 2300, 2470, 2540, 2800 NH⁺, main bands at: 1600, 1440, 1305, 970, 760 and 710.

NMR Spectrum (d₆-DMSO): δH pyrrole protons: 8.40, 7.70, 6.96; δH₂, H₃, H4: 8.40, 7.43; δH C₆H₅: 7.70, 7.43; δH NH⁺: 5.03; δH CH₂: 4.43, 4.16, 3.43

EXAMPLE 12:
6-[4-(4-FLUOROBENZYL)PIPERAZINO]PYRIDO-[3,2-e]PYRROLO[1,2-a]PYRAZINE

The title compound is obtained by carrying out the reaction as in Example 11 but replacing 1-benzylpiperazine in Stage C with 1-(4-fluorobenzyl)piperazine. Recrystallization solvent: acetonitrile Melting point (trihydrochloride): 202° C.

Yield: 63%

Spectral characteristics:

Infrared: ν cm⁻¹ (KBr) 2560, 2850 NH⁺, main bands at: 1610, 1440, 1235, 975, 835 and 770.

NMR Spectrum (d₆-DMSO): δH pyrrole protons: 8.40, 7.20, 6.93; δH₁, H₂, H₃: 8.40, 7.20; δH C₆H₄-F: 7.76, 7.43; δH NH⁺: 5.10; δH CH₂: 4.43, 3.40.

EXAMPLE 13:
6-[4-ALLYLPIPERAZINO)PYRIDO[3,2-e]-PYRROLO[1,2-a]PYRAZINE

The title compound is obtained by carrying out the reaction as in Example 11 but replacing 1-benzylpiperazine in Stage C with 1-allylpiperazine. Recrystallization solvent: acetonitrile Sublimation at 250° C. (trihydrochloride)

Yield: 23%

Spectral characteristics:

Infrared: ν cm⁻¹ (KBr) 2340, 2530 (NH+), main bands at: 1620, 1450, 1310, 980 and 780.

NMR Spectrum (d₆-DMSO): δH pyrrole protons: 8.43, 7.50, 6.96; δH₁, H₂, H₃: 8.43, 7.50; δH(alkyl): 6.00, 5.56; δH NH⁺: 4.20; δH CH₂: 4.20, 3.90 and 3.43.

EXAMPLE 14:
6-(4-BENZYLPIPERAZINO)PYRAZINO[2,3-e]-PYRROLO[1,2-e]PYRAZINE

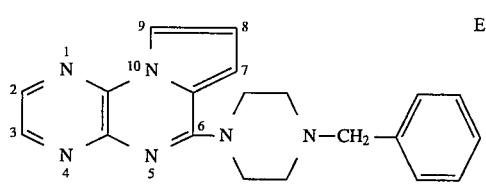

EXAMPLE 14

The title compound is obtained by carrying out the reaction as in Example 1 but replacing 2-(1pyrrolyl)benzoic acid in Stage A' with 3-(1-pyrrolyl)pyrazinoic acid.

Stage A: 5,6-dihydro-6-oxopyrazino[2,3-e]pyrrolo[1,2-a]pyrazine

Melting point: 238° C.

Reference: Lancelot et al., Chem. Pharm. Bull., 1985, Vol. 33, p. 3122

Stage B:
6-chloropyrazino[2,3-e]pyrrolo[1,2-a]pyrazine

Recrystallization solvent: acetonitrile

Melting point: 182° C.

Yield: 21%

Spectral characteristics:

Infrared: ν cm⁻¹ (KBr): main bands at: 1600, 1585, 1270, 780 and 735.

NMR Spectrum (d₆-DM4SO): δH pyrrole protons: 8.66, 7.06, 6.98; δH₂, H₃: 8.28, 8.13.

Stage C:
6-(4-benzylpiperazino)pyrazino[2,3-e]pyrrolo[1,2-a]pyrazine

Recrystallization solvent: acetonitrile

Melting point (trihydrochloride): 200° C.

Spectral characteristics:

Infrared: ν cm⁻¹ (KBr) 2350, 2540 NH⁺, main bands at: 1610, 1440, 1330, 970 and 760.

NMR Spectrum (d₆-DMSO): δH pyrrole protons: 8.48, 7.28, 6.96; δH₂, H₃: 8.48; δH C₆H₅: 7.45; δNH⁺: 5.03, δH CH₂: 4.60, 4.43 and 3.43.

EXAMPLE 15:
6-[4-(4-FLUOROBENZYL)PIPERAZINO]PY-RAZINE[2,3-e]PYRROLO[1,2-a]PYRAZINE

The title compound is obtained by carrying out the reaction as in Example 14 but replacing 1-benzylpiperazine in Stage C with 1-(4-fluorobenzyl)piperazine.

EXAMPLE 16:
7-CHLORO-4-[4-(3,4-METHYLENEDIOXYBEN-ZYL)PIPERAZINO]PYRROLO[1,2-a]QUINOXALINE

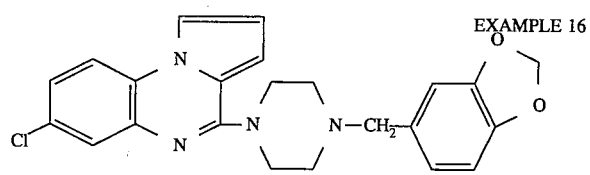

EXAMPLE 16

The title compound is obtained by carrying out the reaction as in Example 3 but replacing 1-benzylpiperazine in Stage C with 1-(3,4-methylenedioxybenzyl)piperazine.

Recrystallization solvent: acetonitrile

Melting point (trihydrochloride): 208° C.

Yield: 67%

Spectral characteristics:

Infrared: ν cm⁻¹ (KBr): 2600, 2700 (NH⁺) main bands at: 1600, 1270, 1040, 820 and 775.

NMR Spectrum (d₆-DMSO): δH pyrrole protons: 8.50, 6.96; δH₆, H₇, H₉: 8.13, 7,36; δH 3,4 methylenedioxybenzyl: 7.36, 6.96; δH CH₂: 3,4-methylenedioxybenzyl: 6.00; δH CH₂: 4.30, 4.00, 3.36; δH NH⁺: 4.90.

EXAMPLE 17 TO 62:

The compounds of the following examples are obtained by following the processes described during Examples 1 to 9 but replacing 1-benzylpiperazine or 1-(4-fluorobenzyl)piperazine in Stages C with the appropriate amines:

EXAMPLE 17: 4-[4-(PYRROLIDINOCARBONYLMETHYL)PIPERAZINO]PYRROLO[1,2-a]QUINOXALINE

EXAMPLE 18: 4-{4-[1-(4-CHLOROPHENYL)-1-PHENYL-METHYL]PIPERAZINO}PYRROLO[1,2-a]QUINOXALINE

EXAMPLE 19: 4-(1,2,5,6-TETRAHYDROPYRID-1-YL)PYRROLO-[1,2-a]QUINOXALINE

EXAMPLE 20: 4-(1,4-THIOMORPHOLINO)PYRROLO[1,2-a]QUINOXALINE

EXAMPLE 21: 4-(4-PHENYLPIPERIDINO)PYRROLO[1,2-a]-QUINOXALINE

EXAMPLE 22: 4-(4-PHENYLPIPERAZINO)PYRROLO[1,2-a]QUINOXALINE

EXAMPLE 23: 4-[4-(3-TRIFLUOROMETHYLPHENYL)PIPERAZINO]PYRROLO[1,2-a]QUINOXALINE

EXAMPLE 24: 4-[4-(ETHOXYCARBONYL)PIPERAZINO]PY-RROLO[1,2-a]QUINOXALINE

EXAMPLE 25: 4-[4-(PYRID-2-YL)PIPERAZINO]PYRROLO[1,2-a]QUINOXALINE

EXAMPLE 26: 4-[4-(2,4-DICHLOROBENZYL)PIPERAZINO]PY-RROLO[1,2-a]QUINOXALINE

EXAMPLE 27: 4-[4-(3,4-DICHLOROBENZYL)PIPERAZINO]-PYRROLO[1,2-a]QUINOXALINE

EXAMPLE 28: 4-[4-(4-CHLOROPHENYL)PIPERAZINO]PYRROLO[1,2-a]QUINOXALINE

EXAMPLE 29: 4-[4-(4-FLUOROPHENYL)PIPERAZINO]PYRROLO[1,2-a]QUINOXALINE

EXAMPLE 30: 4-(4-PROPYLPIPERAZINO)PYRROLO[1,2-a]QUINOXALINE

EXAMPLE 31: 4-(4-ALLYLPIPERAZINO)PYRROLO[1,2-a]QUINOXALINE

EXAMPLE 32: 4-{4-[4,4-BIS(4-CHLOROPHENYL)BUTYL]PIPERAZINO}PYRROLO[1,2-a]QUINOXALINE

EXAMPLE 33: 4-(2,6-DIMETHYLMORPHOLINO)PYRROLO[1,2-a]QUINOXALINE

EXAMPLE 34: 4-{[2-(BENZYLAMINO)ETHYL]AMINO}PYRROLO[1,2-a]QUINOXALINE

EXAMPLE 35: 4-[2,5-DIMETHYLPIPERAZINO]PYRROLO[1,2-a]QUINOXALINE

EXAMPLE 36: 4-(3,3,5-TRIMETHYLPERHYDROAZEPIN-1-YL)PYRROLO[1,2-a]QUINOLALINE

EXAMPLE 37: 4-(PERHYDROAZEPIN-1-YL)PYRROLO[1,2-a]QUINOXALINE

EXAMPLE 38: 4-[4-(4-CHLOROPHENYL)-4-HYDROXYPIPERIDINO]PYRROLO[1,2-a]QUINOXALINE

EXAMPLE 39: 7-CHLORO-4-(4-METHYLPIPERAZINO)PYRROLO[1,2-a]QUINOXALINE

EXAMPLE 40: 8-CHLORO-4-(4-METHYLPIPERAZINO)PYRROLO[1,2-a]QUINOXALINE

EXAMPLE 41: 7-METHYL-4-(4-METHYLPIPERAZINO)PYRROLO[1,2-a]QUINOXALINE

EXAMPLE 42: 7-METHOXY-4-(4-METHYLPIPERAZINO)PYRROLO[1,2-a]QUINOXALINE

EXAMPLE 43: 7-METHYL-4-PIPERAZINOPYRROLO[1,2-a]QUINOXALINE

EXAMPLE 44: 7-CHLORO-4-PIPERAZINOPYRROLO[1,2-a]QUINOXALINE

EXAMPLE 45: 7-CHLORO-4-[4-(PYRROLIDINOCARBONYL-METHYL) PIPERAZINO]PYRROLO[1,2-a]QUINOXALINE

EXAMPLE 46: 7-METHOXY-4-[4-(PYRROLIDINOCARBONYL-METHYL)PIPERAZINO]PYRROLO[1,2-a]QUINOX-ALINE

EXAMPLE 47: 7-CHLORO-4-{4-[1-(4-CHLOROPHENYL)-I-PHENYLMETHYL]PIPERAZINO}PYRROLO[1,2-a]QUINOXALINE

EXAMPLE 48: 8-CHLORO-4-{4-[1-(4-CHLOROPHENYL)-I-PHENYLMETHYL]PIPERAZINO}PYRROLO[1,2-a]QUINOXALINE

EXAMPLE 49: 7-METHYL-4-(1,2,5,6-TETRAHYDROPYRID-1-YL)PYRROLO[1,2-a]QUINOXALINE

EXAMPLE 50: 7-CHLORO-4-(1,4-THIOMORPHOLINO)PYRROLO-[1,2-a]QUINOXALINE

EXAMPLE 51: 7-CHLORO-4-(4-PHENYLPIPERIDINO)PYRROLO-[1,2-a]QUINOXALINE

EXAMPLE 52: 7-METHYL-4-(4-PHENYLPIPERIDINO)PYRROL-0-[1,2-a]QUINOXALINE

EXAMPLE 53: 7-CHLORO-4-(4-PHENYLPIPERAZINO)PYRROLO-[1,2-a]QUINOXALINE

EXAMPLE 54: 7-METHOXY-4-(4-PHENYLPIPERAZINO) PYRROLO-[1,2-a]QUINOXALINE

EXAMPLE 55: 7-CHLORO-4-[4-(3-TRIFLUOROMETHYL-

PHENYL)-PIPERAZINO]PYRROLO[1,2-a]
QUINOXALINE

EXAMPLE 56: 7-CHLORO-4-[4-(ETHOXYCAR-
BONYL)-PIPERAZINO]PYRROLO[1,2-a]QUI-
NOXALINE

EXAMPLE 57: 4-[4-(2,4-DICHLOROBEN-
ZYL)PIPERAZINO]-7-
METHYLPYRROLO[1,2-a]QUINOXALINE

EXAMPLE 58: 7-CHLORO-4-[4-(2,4-DICHLO-
ROBENZYL)-PIPERAZINO]PYRROLO[1,2-a]
QUINOXALINE

EXAMPLE 59: 4-[4-(3,4-DICHLOROBEN-
ZYL)PIPERAZINO]-7-METHOXY-PYRROLO[1,
2-a]QUINOXALINE

EXAMPLE 60: 8-CHLORO-4-[4-(3,4-DICHLO-
ROBENZYL)-PIPERAZINO]PYRROLO[3,2-a]
QUINOXALINE

EXAMPLE 61: 7-CHLORO-4-(4-PROPYLPIPER-
AZINO)PYRROLO-[1,2-a]QUINOXALINE

EXAMPLE 62: 4-(4-ALLYLPIPERAZINO)-7-
CHLOROPYRROLO-[1,2-a]QUINOXALINE

EXAMPLES 63 TO 72:

The compounds of the following examples are obtained
by carrying out the reaction as in Example 11 but replacing
1-benzylpiperazine in Stage C with the appropriately substituted heterocycle:

EXAMPLE 63: 6-(4-METHYLPIPERAZINO)PY-
RIDO[3,2-e]-PYRROLO[1,2-a]PYRAZINE

Melting point: 260° C.

EXAMPLE 64: 6-PIPERAZINOPYRIDO[3,2-e]
PYRROLO[1,2-a]-PYRAZINE

Melting point: 265° C.

EXAMPLE 65: 6-{4-[1-(4-CHLOROPHENYL)-1
-PHENYLMETHYL]-PIPERAZINO}PYRIDO[3,2-
e]PYRROLO[1,2-a]PYRAZINE

EXAMPLE 66: 6-[4-(ETHOXYCARBONYL)PIP-
ERAZINO]PYRIDO-[3,2-e]PYRROLO[1,2-a]
PYRAZINE

Melting point: 196° C.

EXAMPLE 67: 6-(4-PHENYLPIPERIDINO)PY-
RIDO[3,2-e]-PYRROLO[1,2-a]PYRAZINE

EXAMPLE 68: 6-(4-PHENYLPIPERAZINO)PY-
RIDO[3,2-e]-PYRROLO[1,2-a]PYRAZINE

Melting point: 180° C.

EXAMPLE 69: 6-[4-(2,4-DICHLOROBEN-
ZYL)PIPERAZINO]-PYRIDO[3,2-e]PYRROLO[1,
2-a]PYRAZINE

Melting point: 220° C.

EXAMPLE 70: 6-[4-(3,4-DICHLOROBEN-
ZYL)PIPERAZINO]-PYRIDO[3,2-e]PYRROLO[1,
2-a]PYRAZINE

EXAMPLE 71: 6-[4-(4-CHLOROPHENYL)PIPER-
AZINO]PYRIDO[3,2-e]PYRROLO[1,2-a]PYRA-
ZINE

EXAMPLE 72: 6-(4-PROPYLPIPERAZINO)PY-
RIDO[3,2-e]-PYRROLO[1,2-a]PYRAZINE

EXAMPLE 73: 6-(4-BENZYLPIPERAZINO)PY-
RIMIDINO[4,5-e]-PYRROLO[1,2-a]PYRAZINE

EXAMPLE 74: 6-[4-(4-FLUOROBENZYL )PIP-
ERAZINO ]PYRIMIDINO[4,5-e ]PYRROLO[1,2-
a]PYRAZINE

EXAMPLES 75 TO 79:

The compounds of the following examples are obtained
by carrying out the reaction as in Example 1 but replacing
1-benzylpiperazine in Stage C with the appropriate amines:

EXAMPLE 75: 4-[2-(N,N-DIMETHYLAMINO-
)ETHYLAMINO]PYRROLO[1,2-a]QUINOXA-
LINE

EXAMPLE 76: 4-[4-(3-PHENYLPROP-2-EN-1-
YL)PIPERAZINO]PYRROLO[1,2-a]QUINOXA-
LINE

EXAMPLE 77: 4-{4-[2-(2-TRIFLUOROMETH-
YLPHENYL)ETHYL]PIPERAZINO}PYRROLO[1,
2-a]QUINOXALINE

EXAMPLE 78: 4-MORPHOLINOPYRROLO[1,2-
a]QUINOXALINE

EXAMPLE 79: 4-PYRROLIDINOPYRROLO[1,2-
a]QUINOXALINE

EXAMPLE 80: 4-{4-{2-[(METHYLAMINO)SUL-
FONYL]ETHYL}PIPERAZINO}PYRROLO[1,2-a]
QUINOXALINE

EXAMPLES 81 TO 87:

The compounds of the following examples are obtained
by carrying out the reaction as in Example 11 but replacing
1-benzylpiperazine in Stage C with the appropriate amines:

EXAMPLE 81: 6-[2-(N,N-DIMETHYLAMINO-
)ETHYLAMINO]PYRIDO[3,2-e]PYRROLO[1,2-a]
PYRAZINE

EXAMPLE 82: 6-[4-(3-PHENYLPROP-2-EN-1-
YL)PIPERAZINO]PYRIDO[3,2-e]PYRROLO[1,2-
a]PYRAZINE

EXAMPLE 83: 6-{4-[2-(2-TRIFLUOROMETH-
YLPHENYL)ETHYL]PIPERAZINO}PYRIDO[3,2-
e]PYRROLO[1,2-a]PYRAZINE

EXAMPLE 84: 6-MORPHOLINOPYRIDO[3,2-e]
PYRROLO[1,2-a]-PYRAZINE

EXAMPLE 85: 6-PYRROLIDINOPYRIDO[3,2-e]
PYRROLO[1,2-a]PYRAZINE

EXAMPLE 86: 6-THIOMORPHOLINOPYRIDO [3,2-e]PYRROLO[1,2-a]PYRAZINE

EXAMPLE 87: 6-{4-{2-[(METHYLAMINO)SULFONYL ]ETHYL }-PIPERAZINO}PYRIDO[3,2-e] PYRROLO[1,2-a]PYRAZINE

EXAMPLE 88: 8-BENZYLOXY-4-PIPERAZINOPYRROLO[1,2-a]-QUINOXALINE

EXAMPLE 89: 3-[4-(8-BENZYLOXYPYRROLO [1,2-a]-QUINOXALIN-4-YL)PIPERAZINO]PROPIONIC ACID

EXAMPLE 90: 2-METHOXY-6-(4-BENZYLPIPERAZINO)PYRIDO[3,2-e]PYRROLO[1,2-a] PYRAZINE TRIHYDROCHLORIDE

Stage A: 2-amino-6-methoxy-3-nitropyridine 1.65 g (0.0717 mol; 2 equivalents (eq)) of sodium are dissolved in 100 cm$^3$ of methanol. 6.2 g (35.7 mmol) of 2-amino-6-chloro-3-nitropyridine are added and the solution is brought to reflux for 8h. The methanol is evaporated under reduced pressure and the residue is taken up in the minimum amount of water (20 cm$^3$). The solution is extracted with 100 cm$^3$ of ethyl ether. The ether phase is washed with water (20 cm$^3$), separated by settling, dried over MgSO$_4$, decolored with animal charcoal and evaporated on a rotary evaporator to give a 1 st crop. The aqueous phase is extracted under the same conditions with 2 times 50 cm$^3$ of ethyl acetate, giving a 2nd and 3rd crop.

4.7 g (0.0278 mol; yield: 77.7%) of a yellow powder are obtained.

Melting point: 172° C.

Stage B: 6-methoxy-3-nitro-2-(1-pyrrolyl)pyridine 10.45 g (0.0791 mol; 1.2 eq) of 2,5-dimethoxy-tetrahydrofuran and 12.00 g (0.0791 mol; 1.2 eq) of 4chloropyridine hydrochloride are stirred for 10 minutes in 300 cm$^3$ of dioxane. 11.15 g (0.0659 mol) of 2-amino-6methoxy-3-nitropyridine are added and the solution is brought to reflux for 4 h. The dioxane is evaporated under reduced pressure.

The residue is taken up in 250 cm$^3$ of water and then extracted with 500 cm$^3$ of ethyl ether. The ether phase is washed with water, separated by settling, dried over MgSO$_4$, decolored with animal charcoal and concentrated on a rotary evaporator.

11.12 g (0.0507 mol) of an orange powder are obtained.
Yield: 76.9%
Melting point: 70° C.

Stage C: 3-amino-6-methoxy-2-(1-pyrrolyl)pyridine 11.12 g (0.0507 mol) of 6-methoxy-3-nitro-2-(1-pyrrolyl)pyridine are dissolved in 300 cm$^3$ of absolute ethanol.

5 spatulas of Raney nickel (approximately 8 g) are added and then 2 cm$^3$ of hydrazine monohydrate.

The solution is gently heated for 30 minutes and then 28 cm$^3$ of hydrazine monohydrate (in total 0.617 mol; 12.1 eq) are added dropwise over 2 h. The solution is at reflux during this period and for an additional 3 h. After complete cooling, the solution is filtered and then concentrated under reduced pressure to give a brown oil. The Raney nickel precipitate is neutralized with 10N HCl.

The oil can be used directly in the following stage.

8.21 g (0.0434 mol; yield: 85.5%) of oil are obtained.

Stage D: 5,6-dihydro-2-methoxy-6-oxopyrido[3,2-e] pyrrolo[1,2-a]pyrazine 8.21 g (0.0434 mol) of 3-amino-6-methoxy-2-(1pyrrolyl)pyridine are dissolved in 400 cm$^3$ of toluene. 30 cm$^3$ (0.0576 mol; 1.3 eq) of a 20% solution of phosgene in toluene are added and the suspension is brought to reflux for 3 h. A stream of nitrogen is passed over the suspension for 1 h. The precipitate formed is filtered off on sintered glass and gives the expected derivative in the hydrochloride form (melting point: 245° C.). It is taken up in and basified with a saturated NaHCO$_3$ solution. The residual precipitate is filtered off on sintered glass to give 3.4 g of the desired product. The toluene filtrate is concentrated under reduced pressure; the residue is taken up in 100 cm$^3$ of ethyl ether and then filtered off on sintered glass. The precipitate is treated with a saturated NaHCO$_3$ solution and then filtered off on sintered glass to give 3.56 g of final product.

6.96 g (0.323 mol; yield: 74.5%) of cream powder are obtained in total.

Melting point: 250° C.

Stage E: 6-chloro-2-methoxypyrido[3,2-e]pyrrolo[1, 2-2a]pyrazine 2.6 g (0.0120 mol) of 5,6-dihydro-2-methoxy-6-oxopyrido[3,2-e]pyrrolo[1,2-a]pyrazine are added to a solution of 80 cm$^3$ of phosphorus oxychloride and 4 cm$^3$ of pyridine. The solution is brought to reflux for 5 h. After cooling, the phosphorus oxychloride is concentrated under reduced pressure. The residue is taken up in 100 cm$^3$ of ice-cold water and is then gently basified with a 33% aqueous ammonia solution. The precipitate is filtered off on sintered glass. It is extracted with 150 cm$^3$ of ethyl ether and then with 100 cm$^3$ of ethyl acetate. The organic phases are washed with water, dried over MgSO$_4$ and concentrated on a rotary evaporator.

0.94 g (0.0040 mol) of a yellow powder is obtained.
Yield: 33.2%
Melting point: 163° C.

Stage F: 6-(4-benzylpiperazino)-2-methoxypyrido [3,2-e]pyrrolo[1,2-a]pyrazine 0.70 g (0.00397 mol; 1.1 eq) of 1-benzylpiperazine and 0.60 g (0.00434 mol; 1.2 eq) of K$_2$CO$_3$ are added to 20 cm$^3$ of dimethylformamide (DMF). 0.84 g (0.00359 mol) of 6-chloro-2-methoxypyrido[3,2-e]pyrrolo[1,2-a]pyrazine are added and the solution is brought to reflux for 3 h. After cooling, the solution is poured into 100 cm$^3$ of stirred water and extracted with 300 cm$^3$ of ethyl ether. The ether phase is washed with water, dried over MgSO$_4$, decolored with animal charcoal and then concentrated on a rotary evaporator to give the base. The latter is dissolved at 60° C. in 100 cm$^3$ of isopropanol and then 4 cm$^3$ of 10N HCl are rapidly added at ordinary temperature. After stirring for 2 h, the precipitate is filtered off on sintered glass, then rinsed with 50 cm$^3$ of isopropanol and rinsed with 50 cm$^3$ of anhydrous ethyl ether.

0.70 g (0.00143 mol; yield: 40.3%) of a white powder is obtained.

Melting point (trihydrochloride): >264° C. (acetonitrile/isopropanol: 100/40).

IR (KBr v cm$^-$): 3360(NH$^+$), 1610, 1575, 1480, 1270, 995, 695.

$^1$H NMR (d$_6$-DMSO) δ: 8.30 (m, 2H, H$_4$ H$_g$) 7.36–7.43 (m, 6H, C$_6$H$_5$ H$_3$), 6.93 (m, 2H, H$_7$ H$_8$), 4.43–3.42 (m, 13H, CH$_2$ NH$^+$), 3.98 (s, 3H, CH$_3$).

C$_{22}$H$_{23}$N$_5$0.5HCl (MW: 482.822).

EXAMPLE 91: 6-[4-(4-FLUOROBENZYL)PIPERAZINO)-2-METHOXYPYRIDO[3,2-e]PYRROLO[1,2-a]PYRAZINE

The title compound is obtained by carrying out the reaction in the same way as in Example 90 but using 2.00 g (0.00855 mol) of 6-chloro-2-methoxypyrido [3,2-e]pyrrolo [1,2-a]pyrazine, 1.66 g (0.00585 mol) of 1-(4-fluorobenzyl)piperazine, 1.30 g (0.00941 mol; 1.1 eq) of K$_2$CO$_3$ and 30 ml of DMF in Stage F.

Extraction is carried out with 400 cm$^3$ of ethyl ether and the salt is obtained with 4 cm$^3$ of a 10N solution of HCl in isopropanol.

1.25 g (0.00269 mol; yield: 31.4 %) of a pale yellow powder are obtained.

Melting point (dihydrochloride): 210° C. (acetonitrile).

IR (KBr ν cm$^-$): 3380(NH$^+$), 2950, 1610, 1575, 1470, 1275, 990, 750.

1H NMR (d$_6$-DMSO) δ: 8.40-8.28 (m, 2H, H$_4$ H9), 7.75-7.37-7.25 (m, 5H, C$_6$H$_4$ H$_3$), 6.91-6.78 (m, 2H, H$_7$ H$_8$), 4.85 (m, NH$^+$+CH$_2$), 4.47 (M, 4H, pip. CH$_2$), 3.95 (s, 3H, CH$_3$), 3.45 (m, 4H, pip. CH$_2$).

C$_{22}$H$_{22}$FN$_5$0.2HCl (464.353)

EXAMPLE 92: 2-BENZYLOXY-6-(4-BENZYLPIPERAZINO)PYRIDO[3,2-e]PYRROLO[1,2-a]PYRAZINE

Stage A: 2-amino-6-benzyloxy-3-nitropyridine 1.64 g (0.0713 mol; 1.2 eq) of sodium are placed in 150 cm$^3$ of toluene and then 7.73 g (0.0713 mol; 1.2 eq) of benzyl alcohol. After complete dissolution, 10.34 g (0.0595 mol) of 2-amino-6-chloro-3-nitropyridine are added, the heating is progressively increased over 30 minutes and the solution is then refluxed for 3 h. After cooling, 50 cm$^3$ of water are added and the toluene is removed under reduced pressure. The residual solution is extracted with 400 cm$^3$ of ethyl ether. The ether phase is separated by settling, dried over MgSO$_4$, decolored with animal charcoal and concentrated on a rotary evaporator.

The semi-solid residue is taken up in 20 cm$^3$ of ethyl ether and filtered off on sintered glass, where the solid product is recovered.

6.73 g (0.0274 mol; yield: 46.0%) of an orange powder are obtained. Melting point: 134° C. (ethyl ether).

Stage B: 6-benzyloxy-3-nitro-2-(1-pyrrolyl)pyridine 8.2 g (0.062 mol; 1.2 eq) of 2,5-dimethoxytetrahydrofuran are stirred for 10 minutes in 200 cm$^3$ of glacial acetic acid. 12.68 g (0.0517 mol) of 2-amino-6benzyloxy-3nitropyridine are added and the solution is brought to reflux for 4 h. The acetic acid is removed under reduced pressure. The residue is basified with 200 cm$^3$ of a saturated NaHCO$_3$ solution and then extracted with 400 cm$^3$ of ethyl ether. The ether phase is washed with water, dried over MgSO$_4$, decolored with animal charcoal and concentrated under reduced pressure.

8.48 g (0.0287 mol; yield: 55.5%) of a red powder are obtained. Melting point: 130° C. (ethyl ether)

Stage C: 3-amino-6-benzyloxy-2-(1-pyrrolyl)pyridine 6.41 g (0.0241 mol; yield: 91.3%) of a brown oil corresponding to the title compound are obtained by carrying out the reaction in the same way as in Stage C of Example 90 but using 7.8 g (0.0264 mol) of 6-benzyloxy-3-nitro-2-(1-pyrrolyl) pyridine, 4 spatulas (approximately 7 g) of Raney nickel and 10 cm$^3$ (0,206 mol; 7.8 eq) of hydrazine monohydrate.

Stage D: 5,6-dihydro-2-benzyloxy-6-oxopyrido[3,2-e]pyrrolo[1,2-a]pyrazine 2.73 g (0.0094 mol; yield: 38.8%) of a beige powder are obtained by carrying out the reaction in the same way as in Stage D of Example 90 but without concentrating the toluene filtrate and while using 6.04 g (0.0241 mol) of 3-amino-6-benzyloxy-2-(1-pyrrolyl)pyridine, 15 cm$^3$ (0.0288 mol; 1.2 eq) of COCl$_2$/toluene and 250 cm$^3$ of toluene.

Melting point: 264° C.

Stage E: 2-benzyloxy-6-chloropyrido[3,2-e]pyrrolo[1,2-a]pyrazine 1.47 g (0.0047 mol; yield: 52.1%) of a brown powder are obtained by carrying out the reaction in the same way as in Stage E of Example 90 but using 2.65 g (0.0091 mol) of 5,6-dihydro-2-benzyloxy-6-oxopyrido[3,2-e]pyrrolo[1,2-a] pyrazine, 10 cm$^3$ of pyridine and 100 cm$^3$ of POCl$_3$.

Melting point: 106° C. (ethyl acetate).

Stage F: 2-benzyloxy-6-(4-benzylpiperazino)pyrido [3,2-e]pyrrolo[1,2-a]pyrazine The title compound is obtained by carrying out the reaction in the same way as in Stage F of Example 90 but using 1.00 g (0.00322 mol) of 2-benzyloxy-6-chloropyrido [3,2-e]pyrrolo[1,2-a]pyrazine and 0.54 g (0.00387 mol; 1.2 eq) of K$_2$CO$_3$.

In order to form the salt, the base is taken up in 60 cm$^3$ of acetone, 1.1 eq of fumaric acid (0.41 g) are added and the suspension is heated for 15 minutes. After cooling, the precipitate is filtered off on sintered glass and then rinsed with 30 cm$^3$ of anhydrous ethyl ether. 0.88 g (0.0015 mol; yield: 48.1%) of a white powder is obtained.

Melting point (monofumarate): 208° C. (acetonitrile)

IR (KBr ν cm$^{-1}$): 1670 (CO), 1430, 1270, 1230, 1010, 930, 650.

$^1$H NMR (d$_6$-DMSO) δ: 7.80 (t, 1H, H$_9$), 7.47 (d, 1H, H$_4$), 7.00 (m, 10H, 2 C$_6$H$_5$), 6.60-6.50 (m, 3H, H$_3$ H$_7$ H$_8$), 6.27 (s, 2H, CH fumarate), 5.27 (s, 2H, CH$_2$O), 4.20 (s, 2H, CH$_2$, 3.40-2.63-2.17 (m, 8H, piperazine CH$_2$).

C$_{28}$H$_{27}$N$_5$O.C$_4$H$_4$O$_4$ (565.603).

EXAMPLE 93: 2,6-BIS(4-BENZYLPIPERAZINO)PYRIDO[3,2-e]PYRROLO[1,2-a]PYRAZINE

Stage A: 6-chloro-3-nitro-2-(1-pyrrolyl)pyridine

The reaction is carried out in the same way as in Stage B of Example 90 but starting from 15.40 g (0.0887 mol) of 6-chloro-3-nitro-2-aminopyridine and by using 12.9 g (0.0976 mol; 1.1 eq) of 2,5-dimethoxytetrahydrofuran, 14.64 g (0.0976 mol; 1.1 eq) of 4-chloropyridine hydrochloride and 300 cm$^3$ of 1,4-dioxane. The solution is brought to reflux for 6 h. At the end of the reaction, the precipitate is taken up in ethyl ether.

The insoluble material is filtered (melting point: 192° C.) and the ether solution is concentrated under reduced pressure to provide the expected derivative.

10.27 g (0.0459 mol; yield: 51.7%) of a red powder are obtained.

Melting point: 110° C.

Stage B: 3-amino-6-chloro-2-(1-pyrrolyl)pyridine 9.27 g (0.0414 mol) of 6-chloro-3-nitro-2-(1-pyrrolyl)pyridine are dissolved in 300 cm$^3$ of 95% ethanol. 115.25 g (0.414 mol; 10 eq) of iron sulfate heptahydrate are added, then 0.5 cm$^3$ of 10N HCl and finally 5 cm$^3$ of water. The solution is brought to reflux while adding, during the first 20 minutes, 57 cm$^3$ of aqueous ammonia solution in order to maintain the pH at greater than 7.

Reflux is maintained for 1 h while adding 6 cm$^3$ of aqueous ammonia. After cooling, the ethanol is removed on a rotary evaporator. The residue is taken up in 100 cm$^3$ of water and extracted with 200 cm$^3$ of ethyl ether. The ether phase is washed with water, separated by settling, dried over MgSO$_4$, decolored with animal charcoal and concentrated on a rotary evaporator to give a 1st crop.

The aqueous phase, basified with NH$_4$OH, is extracted with 200 cm$^3$ of ethyl acetate. The organic phase, treated in the same way as the ether phase, gives a 2nd crop.

4.59 g (0.0237 mol; yield: 57.1%) of a beige powder are obtained.

Melting point: 89° C. (ethyl ether/hexane: 80/20).

Stage C: 5,6-dihydro-2-chloro-6-oxopyrido[3,2-e] pyrrolo[1,2-a]pyrazine 2.6 g (0.0118 mol) of gray powder are obtained by carrying out the reaction in the same way as in Stage D of Example 90 but without concentrating the toluene filtrate and while using 4.59 g (0.0237 mol) of 3-amino-6-chloro-2-(1-pyrrolyl)pyridine, 12.5 cm$^3$ (0.0240 mol; 1 eq) of COCl$_2$/toluene and 200 cm$^3$ of toluene.

Yield: 49.9%

Melting point: 270° C.

Stage D: 2,6-dichloropyrido[3,2-e]pyrrolo[1,2-a] pyrazine 1.27 g (0.00533 mol; yield: 45.0%) of a yellow powder are obtained by carrying out the reaction in the same way as in Stage E of Example 90 but starting from 2.6 g (0.0118 mol) of 5,6-dihydro-2-chloro-6-oxopyrido[3,2-e]pyrrolo[1,2-a]pyrazine and using 100 cm$^3$ of POCl$_3$ and 7 cm$^3$ of pyridine.

Melting point: 211° C. (ethyl acetate)

Stage E: 2,6-bis(4-benzylpiperazino)pyrido[3,2-e] pyrrolo[1,2-a]pyrazine 1.37 g (0.00206 mol; yield: 37.8%) of yellow powder are obtained by carrying out the reaction in the same way as in Stage F of Example 90 but starting from 1.30 g (0.00546 mol) of 2,6-dichloropyrido[3,2-e]pyrrolo[1,2-a]pyrazine and using 2.12 g (0.0120 mol; 2.2 eq) of 1-benzylpiperazine, 1.89 g (0.0137 mol; 2.5 eq) of K$_2$CO$_3$ and 30 cm$^3$ of DMF, and bringing the solution to reflux for 4 h.

Melting point (tetrahydrochloride): 210° C. (acetonitrile)

IR (KBr ν cm$^{-1}$): 3350, 1470, 1150, 1050, 730, 700.

Mass spectrum: Molecular peak at 517 (m/e); C$_{32}$H$_{35}$N$_7$.4HCl (663.493).

$^1$H NMR (d$_6$-DMSO): Product insoluble in DMSO.

EXAMPLE 94: 6-(4-BENZYLPIPERAZINO)-4-METHYL-PYRIDO[3,2-e]PYRROLO[1,2-a]PYRAZINE

Stage A: 4-methyl-3-nitro-2-(1-pyrrolyl)pyridine 11.82 g (0.0581 mol; yield: 90.4%) of a yellow powder, which turns red in air, are obtained by carrying out the reaction in the same way as in Stage B of Example 92 but starting from 9.85 g (0.0643 mol) of 4-methyl-3nitro-2-aminopyridine and using 10.2 g (0.0772 mol; 1.2 eq) of 2,5-dimethoxytetrahydrofuran and 200 cm$^3$ of glacial CH$_3$CO$_2$H, and bringing the solution to reflux for 3 h.

Melting point: 63° C.

20 Stage B: 3-amino-4-methyl-2-(1-pyrrolyl)pyridine 8.73 g (0.0500 mol; yield: 86.6%) of a green powder are obtained by carrying out the reaction in the same way as in Stage C of Example 90 but starting from 11.82 g (0.0581 mol) of 4-methyl-3-nitro-2-(1-pyrrolyl)pyridine and using 5 spatulas (≅8 g) of Raney nickel, 20 cm$^3$ (0.411 mol; 7 eq) of hydrazine monohydrate and 300 cm$^3$ of ethanol.

Melting point: 77° C. (ethyl ether)

Stage C: 5,6-dihydro-4-methyl-6-oxopyrido[3,2-e] pyrrolo[1,2-a]pyrazine 7.8 g (0.0392 mol; yield: 77.6%) of a beige powder are obtained by carrying out the reaction in the same way as in Stage D of Example 92 but starting from 8.73 g (0.050 mol) of 3-amino-4-methyl-2-(1-pyrrolyl)pyridine and using 30 cm$^3$ (0.0576 mol; 1.15 eq) of COCl$_2$/toluene and 250 cm$^3$ of toluene.

Melting point: >264° C.

Stage D: 6-chloro-4-methylpyrido[3,2-e]pyrrolo [1,2-a]pyrazine 5.83 g (0.0268 mol) of a yellow powder are obtained by carrying out the reaction in the same way as in Stage E of Example 90 but starting from 7.8 g (39.2×10$^{-3}$ mol) of 5,6-dihydro-4-methyl-6-oxopyrido [34,2-e]pyrrolo[1,2-a]pyrazine and using 150 cm$^3$ of POCl$_3$ and 10 cm$^3$ of pyridine.

Yield: 68.4%

Melting point: 139° C. (ethyl acetate)

Stage E: 6-(4-benzylpiperazino)-4-methylpyrido[3, 2-e]pyrrolo[1,2-a]pyrazine The solution is extracted with ethyl ether and then with ethyl acetate by carrying out the reaction in the same way as in Stage F of Example 90 but starting from 2.00 g (0.0092 mol) of 6-chloro-4-methylpyrido[3,2-e]pyrrolo[1,2-a]pyrazine and using 1.78 g (0.0101 mol; 1.1 eq) of 1-benzylpiperazine, 1.52 g (0.011 mol; 1.2 eq) of K$_2$CO$_3$ and 30 cm$^3$ of DMF.

3.00 g (0.00697 mol; yield: 75.8%) of a yellow powder are obtained.

Melting point (dihydrochloride): 240° C. (acetonitrile/isopropanol: 60/40).

IR (KBr ν cm$^{-1}$): 3400(NH$^+$), 3080, 2440, 1480, 1430, 1260, 1110, 955, 830.

$^1$H NMR (d$_6$-DMSO) δ: 8.30 (t, 1H, H$_9$), 8.18 (d, 1H, H$_2$), 7.67-7.46 (m, 5H, C$_6$H$_5$), 7.30 (d, 1H, H$_3$), 7.10 (t, 1H, H$_8$), 6.83 (t, 1H, H$_7$), 4.28-3.40 (m, 10H, CH$_2$), 2.60 (s, 3H, CH$_3$), 11.93 (m, NH$^+$).

C$_{22}$H$_{23}$N$_5$.2HCl (430.461)

EXAMPLE 95: 6-[4-(4-FLUOROBENZYL)PIPER-AZINO-4-METHYL-PYRIDO[3,2-e]PYRROLO[1,2-a]PYRAZINE 3.34 g (0.00745 mol; yield: 81.0%) of a yellow powder are obtained by carrying out the reaction in the same way as for Example 94 but using 1.96 g (0.0101 mol; 1.1 eq) of 1-(4-fluorobenzyl)piperazine, 1.52 g (0.011 mol; 1.2 eq) of K$_2$CO$_3$ and 30 cm$^3$ of DMF in Stage E and then extracting the solution with ethyl ether and then with ethyl acetate. Melting point (dihydrochloride): 228° C.

IR (KBr ν cm$^{-1}$): 3440 (NH$^+$), 1505, 1435, 1260, 1160, 950.

1H NMR (d$_6$-DMSO) δ: 8.27 (t, 1H, H9), 8.13 (d, 1H, H2), 7.73 (t, 2H, C$_6$H$_4$), 7.27 (m, 3H, H$_3$ C$_6$H$_4$), 7.06 (t, 1H, H$_8$), 6.80 (t, 1H, H$_7$), 5.40 (s, NH$^+$), 4.40-3.70-3.36 (m, 10H, CH$_2$), 2.56 (s, 3H, CH$_3$).

C$_{22}$H$_{22}$FN$_5$.2HCl (448.353)

EXAMPLE 96: 6-[4-(3,4-METHYLENEDIOXY-BENZYL)PIPER-AZINO]PYRIDO[3,2-e]PYR-ROLO[1,2-a]PYRAZINE 1.13 g (0.00227 mol; yield: 46.3%) of a white powder are obtained by carrying out the reaction in the same way as in Stage F of Example 90 but starting from 1.00 g (0.00491 mol) of 6-chloropyrido[3,2-e]pyrrolo [1,2-a]pyrazine, described in Stage B of Example 11, and using 1.19 g (0.0054 mol; 1.1 eq) of N-(3,4-methylenedioxybenzyl)piperazine, 0.82 g (0.059 mol; 1.2 eq) of K$_2$CO$_3$ and 30 cm$^3$ of DMF.

Melting point (trihydrochloride): 220° C.

IR (KBr ν cm$^{-1}$): 3400(NH$^+$), 1605, 1475, 1425, 1290, 1250, 1030, 930, 770. $^1$H ν NMR (d$_6$-DMSO) δ: 8.40 (m, 3H, H$_2$ H$_9$ H$_4$), 7.33-6.97 (m, 6H, H$_3$ H$_7$ H$_8$)C$_6$H$_3$), 6.03 (s, 2H, CH$_2$O), 5.27 (m, NH$^+$), 4.65-4.33-3.98-3.43 (m, 10H, CH$_2$).

C$_{22}$H$_{21}$N$_5$O$_2$.3HCl (496.806).

EXAMPLE 97: 4-(PERHYDRO-1,4-DIAZEPIN-1-YL)PYRROLO-[1,2-a]QUINOXALINE 1.6 g (0.00789 mol) of 4-chloropyrrolo [1,2-a]quinoxaline and 7.9 g (0.00789 mol; 10 eq) of homopiperazine are finely powdered and are then introduced into a round-bottomed flask at 180° C. The reaction mixture is maintained at reflux for 5 h. 100 cm$^3$ of water are then cautiously added and the round-bottomed flask is cooled in an ice bath. The precipitate formed is filtered off on sintered glass and then taken up in 200 cm$^3$ of ethyl ether. The ether phase is washed with water, separated by settling, dried over MgSO$_4$, decolored with animal charcoal and concentrated under reduced pressure to give the base.

The latter is taken up in 100 cm$^3$ of isopropanol at 60° C. 3 cm$^3$ of 10N HCl are rapidly added dropwise at 25° C. After stirring for 1 h, the precipitate is filtered off on sintered glass and rinsed with 40 cm$^3$ of isopropanol and then with 40 cm$^3$ of anhydrous ethyl ether.

0.74 g (0.00207 mol; yield: 26.2%) of a white powder is obtained.

Melting point (dihydrochloride): 196° C. (acetonitrile).

IR (KBr ν cm$^{-1}$): 3030-2740 (NH$^+$), 1510, 1430, 1150, 930, 730.

Mass spectrum: Molecular peak m/e=26;

C$_{16}$H$_{18}$N$_4$.2HCl.H$_2$O (357.270).

PHARMACOLOGICAL STUDY OF THE COMPOUNDS OF THE INVENTION

EXAMPLE A: STUDY OF THE BINDING OF THE COMPOUNDS OF THE INVENTION TO RECEPTORS

A-1: Study of the binding to 5-HT$_3$ serotoninergic receptors

Binding of the compounds of the invention to 5-HT$_3$ receptors was determined according to standard affinity measurement techniques.

PROTOCOL:

BRL 43694 is used as radioligand, ICS 205 930, at 10$^{-5}$M, is used as nonspecific ligand and tractus solitarius rings (TSR) and NG 108-15 cells are used as tissues.

A-2: Study of the binding of the compounds of the invention to 5-HT$_{1A}$, 5-HT$_{1B}$, 5-HT$_{1C}$, 5-HT$_{1D}$ and 5HT$_2$ serotoninergic receptors.

Binding of the compounds of the invention is measured, according to conventional methods:

for 5-HT$_{1A}$ receptors, by the displacement of 8-OH-DPAT in pig hippocampus and frontal cortex homogenates, for 5-HT$_{1B}$ receptors, by the displacement of 5-hydroxytryptamine from rat globus pallidus, striatum and cortex homogenates, for 5-HT$_{1C}$ receptors, by the displacement of N-methylmesulergine and 10$^{-6}$M of spiperone in pig choroid plexus homogenates, for 5-HT1D receptors, by the displacement of 5-OH-tryptamine in pig globus pallidus, striatum and cortex homogenates, for 5-HT$_2$ receptors, by the displacement of ketanserin in calf frontal cortex homogenates.

CONCLUSION:

It appears that the compounds of the invention have a very high affinity for 5-HT$_3$ receptors. The compounds of the invention also turn out to possess a high selectivity for 5HT$_3$ receptors with respect to the other serotoninergic receptors to which they are not bound.

EXAMPLE B: MEASUREMENT OF THE ACCUMULATION OF $^{14}$-CGUANIDINIUM IN NG 108-15 CELLS

The accumulation of $^{14}$-C-guanidinium in NG 108-15 cells is measured and makes it possible to study the interaction of the tested compounds with 5-HT$_3$ receptors, knowing that this accumulation is stimulated by agonists of 5-HT$_3$ receptors.

The NG 108-15 hybrid clone (neuroblastoma-glioma) is cultured under standard conditions (Dulbecco's medium to which 40 mM of sodium bicarbonate, 1.8 mM of L-glutamine, 0.1 mM of hypoxanthine, 1 μM of aminopterin, 16 μM of thymine and 10% of fetal calf serum are added) at 37° C. in an atmosphere enriched in $CO_2$ (7%). At confluence ($\cong 3.5 \times 10^5$ cells in dishes with diameters of 35 mm), the culture medium is sucked off and the cell lawn is rapidly washed with 3 cm$^3$ of a HEPES (20 mM) buffer containing 145 mM of NaCl, 5.4 mM of KCl, 1.8 mM of $CaCl_2$, 1.0 mM of $MgCl_2$ and 20 mM of glucose, pH 7.4. After removing the washing solution, pouring is gently carried out, into each culture dish, of 1.5 cm$^3$ of the same buffer (except that the NaCl concentration is brought to 135 mM) to which has been added 10 mM of guanidinium chloride plus 100–250 nCi of $^{14}$-C-guanidinium, 10 μM of Substance P and an agonist of 5-HT$_3$ receptors in the presence or in the absence of the compound to be tested. The incubation lasts 10 minutes at 37° C. The medium is then sucked off and the cells are rapidly washed twice with 3 cm$^3$ of the washing buffer in which the NaCl has been fully replaced by an equimolar concentration of choline chloride. Finally, the cell lawn is taken up in 0.5 cm$^3$ of 0.4N sodium hydroxide solution and the accumulated radioactivity is counted by spectrometry in liquid medium (Aquasol).

Under these experimental conditions, agonists of 5-HT$_3$ receptors (10 μM-0.1 mM), such as serotonin, 2-methyl-5-hydroxytryptamine and phenylbiguanide, multiply the intracellular accumulation of $^{14}$-C-guanidinium by 5 and this effect can be completely suppressed with 10–100 nM of a selective 5-HT$_3$ antagonist (ondansetron, zacopride).

This test has made it possible to show that some compounds of the invention are powerful agonists of 5-HT$_3$ receptors. Additionally, other compounds of the invention, agonists if they are tested alone, are revealed to be antagonists in the presence of serotonin.

The following table illustrates the effects of the compounds of the invention:

| COMPOUNDS | $EC_{50}$ (50% effective concentration) |
|---|---|
| (Example 11) | 30 nM (Agonist) |
| (Example 3) | 50 nM (Agonist) |
| (Example 4) | 100 nM (Agonist) Antagonist effect at 3 nM |
| (Example 1) | ≈100 nM (Agonist) |

EXAMPLE C: BRADYCARDIC BEZOLD-JARISCH REFLEX

Bradycardia (Bezold-Jarisch reflex) is induced by the intravenous injection of 5-HT$_3$ serotonin in rats anesthetized with urethane.

This response consists of a violent but transitory bradycardia induced by stimulation of 5-HT$_3$ receptors on vagal afferent neurons. This model is thus entirely appropriate for revealing possible agonist or antagonist effects of compounds which are potential ligands of 5-HT$_3$ receptors.

PROTOCOL:

The animal (adult male rat, Sprague-Dawley strain, 250–300 g) is first of all anesthetized with urethane (1.4 g/kg i.p.) and then a tracheotomy is performed in order to implant a tracheal cannula. A catheter (0.3 mm) is introduced into the abdominal aorta via the femoral artery for the continuous recording of the arterial pressure and the cardiac rhythm. The pharmacological agents are injected into the vena saphena which has had a cannula inserted for this purpose. The i.v. injection of 30 μg of serotonin, of 2-methyl-5-hydroxytryptamine or of phenylbiguanide leads to a violent (−80%) and transitory (for approximately 4–5 seconds) fall in the cardiac rhythm and this effect can be completely prevented by the prior administration (i.v.) of various selected antagonists such as zacopride or ondansetron (at a dose of 1 μg/kg).

REFERENCE:

Drugs of the Future, 1992, 17(8), 660–664.

RESULTS:

It appears, in this test, that the compounds of the invention behave as powerful ligands of 5-HT$_3$ receptors and have an either antagonist or partial agonist action.

The following table illustrates the activity of the compounds of the invention:

| COMPOUNDS | Agonist Effect | | Antagonist Effect |
|---|---|---|---|
| | Dose (I.V.) | Bradycardia % | IC$_{50}$ (I.V.) |
| Serotonin | 30 μg · Kg$^{-1}$ | 68.0 ± 2.3 (n = 21) | |
| 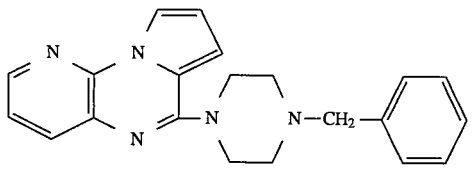 (Example 11) | 120 μg · Kg$^{-1}$ | 59.4 ± 7.2 (n = 5) | Antagonist effect at 120 μg · Kg$^{-1}$ |
| 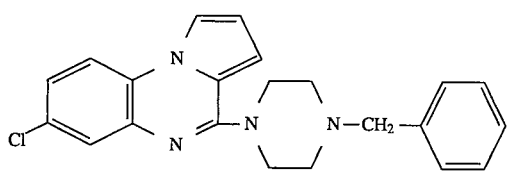 (Example 3) | 30 μg · Kg$^{-1}$ 60 μg · Kg$^{-1}$ 120 μg · Kg$^{-1}$ | 0 | 31.2 μg · Kg$^{-1}$ |
| 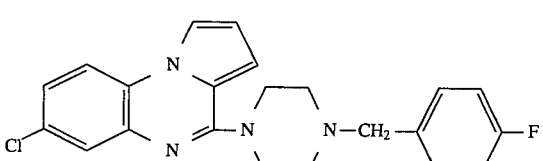 (Example 4) | 30 μg · Kg$^{-1}$ 60 μg · Kg$^{-1}$ 120 μg · Kg$^{-1}$ | 0 | 75.4 μg · Kg$^{-1}$ |
| 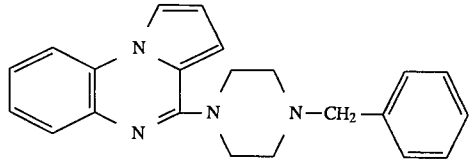 (Example 1) | | | 60 μg · Kg$^{-1}$ |

Bradycardia is expressed as percentage of lowering (maximum) of the base rhythm, before any treatment (means±M.S.D.).

EXAMPLE E: PHARMACEUTICAL COMPOSITION: TABLETS

Tablets containing a 1 mg dose of 4-(4-benzylpiperazino)pyrrolo[1,2-a]quinoxaline Formula for the preparation of 1000 tablets:

| | |
|---|---|
| 4-(4-benzylpiperazino)pyrrolo[1,2-a]quinoxaline | 1 g |
| Wheat starch | 2.5 g |
| Maize starch | 1.5 g |
| Lactose | 8.5 g |
| Magnesium stearate | 0.2 g |
| Silica | 0.1 g |
| Hydroxypropyl cellulose | 0.2 g |

We claim:

1. A compound which is selected from those of formula (I):

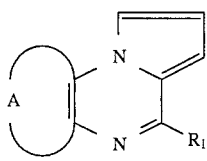

in which:

R¹ represents a group of formula:

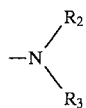

in which $R_2$ and $R_3$ form, with the nitrogen atom which carries them, a group chosen from:

piperazine, substituted piperazine, piperidine, substituted piperidine, pyrrolidine, substituted pyrrolidine, morpholine, morpholine substituted by one more alkyl groups, tetrahydropyridine, thiomorpholine, a 5- to 12-membered azaspiro radical, a 5- to 12-membered azaspiro radical substituted by one or more alkyl or oxo groups, a 7- to 12-membered mono- or bicyclic azacycloalkyl radical optionally including, in its skeleton, to 1 or 2 additional heteroatoms chosen from oxygen, sulfur, and nitrogen, a 7- to 12-membered mono- or bicyclic azacycloalkyl radical, substituted by one or more alkyl or oxo groups, optionally including, in its skeleton, to 1 or 2 additional heteroatoms chosen from oxygen, sulfur, and nitrogen, a group —NH—(CH$_2$)$_k$—NH$_2$ in which k represents 2, 3 to 4, and a substituted group —NH—(CH$_2$)$_k$—NH$_2$ in which k is as defined above, and A forms, with the 2 carbon atoms to which it is bonded, a ring chosen from benzo, pyrido, pyrazino and pyrimidino; A being unsubstituted or substituted by one or more radicals chosen from:

alkyl, hydroxyl, alkoxy, acyl, alkoxycarbonyl, halogen, trifluoromethyl,

—(CH$_2$)$_m$-phenyl and —O—(CH$_2$)$_m$-phenyl in which the phenyl ring is itself unsubstituted or substituted by one or more radicals chosen from halogen, alkyl, alkoxy, hydroxyl and trifluoromethyl; and m represents 0 or 1 to 4, —(CH$_2$)$_m$-piperazine in which the piperazine group is itself substituted or unsubstituted and m is as defined above, provided that if A forms, with the 2 carbon atoms to which it is bonded, a benzo ring, then $R_2$ and $R_3$ cannot form, with the nitrogen atom which carries them, piperazine which is unsubstituted or substituted by alkyl, phenyl or alkyl-substituted phenyl, morpholine or aminoalkylamines, it being understood that the term "substituted", as it relates to the piperazine, piperidine, pyrrolidine and —NH—(CH$_2$)$_k$—NH$_2$ groups, means that these groups can be substituted by one or more halogen, hydroxyl, oxo, $R_4$ radicals or radicals

with $R_4$ being chosen from:

alkyl, alkoxy, alkenyl which is unsubstituted or substituted by a phenyl which is itself unsubstituted or substituted by one or more radicals chosen from halogen, alkyl, alkoxy, hydroxyl and trifluoromethyl,

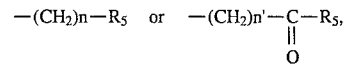

where n represents 0 or 1 to 5, n' represents 1 to 5, and where $R_5$ represents a radical chosen from phenyl, benzhydryl, thienyl, pyrrolyl, pyrrolidinyl, furyl, pyrimidinyl, pyridyl, methylenedioxyphenyl, ethylenedioxyphenyl, naphthyl, quinolyl, isoquinolyl, cycloalkyl and dicycloalkylmethyl; the term "cycloalkyl" meaning a 3- to 12-membered mono- or bicyclic group, it being possible for these R5 radicals themselves to be substituted by one or more of radicals chosen from halogen, trifluoromethyl, carboxyl, hydroxyl, alkyl and alkoxy, and (CH$_2$)$_n$'—$R_6$ where n' is as defined above and $R_6$ represents a group chosen from carboxyl, alkoxycarbonyl, amino, alkylamino, dialkylamino, —SO$_2$NR$_7$R$_8$ and —CONR$_7$R$_8$ in which $R_7$ and $R_8$ represent, each independently of the other, a hydrogen atom or an alkyl group, its optical isomers, and its addition salts with a pharmaceutically acceptable acid or base, it being understood that, except when otherwise specified, the terms "alkyl", "alkoxy" and "acyl" represent linear or branched groups having from 1 to 6 carbon atoms, inclusive, and the term "alkenyl" represents a linear or branched unsaturated group having from 2 to 6 carbon atoms, inclusive.

2. A compound of claim 1 which is selected from those in which A forms a benzo ring with the 2 carbon atoms to which it is bonded, its optical isomers, and its addition salts with a pharmaceutically-acceptable acid or base.

3. A compound of claim 1 which is selected from those in which A forms a pyrido ring with the 2 carbon atoms to which it is bonded, its optical isomers, and its addition salts with a pharmaceutically-acceptable acid or base.

4. A compound of claim 1 which is selected from those in which $R_2$ and $R_3$ form, with the nitrogen atom which carries them, a piperazine which is substituted in the 4-position by a benzyl radical which is itself unsubstituted or substituted, its optical isomers, and its addition salts with a pharmaceutically-acceptable acid or base.

5. A compound as claimed in claim 1 which is selected from 4-(4-benzylpiperazino)pyrrolo[1,2-a]quinoxaline and an addition salt, therefore with a pharmaceutically acceptable acid.

6. A compound as claimed in claim 1 which is selected from 4-(4-benzylpiperazino)-7-chloropyrrolo[1,2-a]quinoxaline and an addition salt, therefore with a pharmaceutically-acceptable acid.

7. A compound as claimed in claim 1 which is selected from 7-chloro-4-[4-(3,4-methylenedioxybenzyl) piperazino] pyrrolo[1,2-a]quinoxaline and an addition salt, therefore with a pharmaceutically-acceptable acid.

8. A compound as claimed in claim 1 which is selected from 6-(4-benzylpiperazino)pyrido[3,2-e]pyrrolo[1,2-a]pyrazine and an addition salt, therefore with a pharmaceutically-acceptable acid.

9. A compound as claimed in claim 1 which is selected from 6-(4-allylpiperazino) pyrido[3,2-e]pyrrolo[1,2-a]pyrazine and an addition salt, therefore with a pharmaceutically-acceptable acid.

10. A compound as claimed in claim 1 which is selected from 6-[4-(3,4-methylenedioxybenzyl) piperazino]pyrido[3,2-e]pyrrolo[1,2-a]pyrazine and an addition salt, therefore with a pharmaceutically-acceptable acid.

11. A compound as claimed in claim 1 which is selected from 6-piperazinopyrido[3,2e]pyrrolo[1,2-a]pyrazine and an addition salt, therefore with a pharmaceutically-acceptable acid.

12. A compound as claimed in claim 1 which is selected from 6-(4-methylpiperazino)pyrido[3,2-e]pyrrolo[1,2-a]pyrazine and an addition salt, therefore with a pharmaceutically-acceptable acid.

13. A compound as claimed in claim 1 which is selected from 4-[4-(4-fluorobenzyl)piperazino]-7-methoxypyrrolo[1,2-a]quinoxaline and an addition salt, therefore with a pharmaceutically-acceptable acid.

14. A pharmaceutical composition useful for treating a disorder linked to the 5-$HT_3$ receptors containing, as active principle, a compound of claim 1, in combination with a pharmaceutically-acceptable excipient or vehicle.

15. A method of treating a mammal afflicted with a disorder linked to the 5-$HT_3$ receptors comprising the step of administering to the said mammal an amount of a compound as claimed in claim 1 which is effective for alleviation of said disorder.

* * * * *

UNITED STATES PATENT AND TRADEMARK OFFICE
CERTIFICATE OF CORRECTION

PATENT NO. : 5,599,812
DATED : February 4, 1997
INVENTOR(S) : S. Rault; J-C Lancelot; H. Prunier; M. Robba; P. Delagrange; P. Renard; G. Adam Page 1 of 7

It is certified that error appears in the above-indentified patent and that said Letters Patent is hereby corrected as shown below:

Title Page, Column 2, [56] References Cited, PUBLICATIONS, line 3: "columbus" should read -- Columbus --.

Column 2, line 61: Insert -- O or -- between "represents" and "an".

Column 5, line 33: "R1" should read -- $R_1$ --.

Column 6, line 49: "δSH" should read -- δH --.

Column 6, line 55: Delete the "-" at the end of the line and Insert -- ) --. Page 8, line 13

Column 6, line 56: Delete the ")" at the beginning of the line.

Column 7, line 22: "H9" should read -- $H_9$ --. Page 9, line 3

Column 7, line 48: After "($d_6$-DMSO):", line should read -- δH $C_6H_5$: 7.47; δH $C_6H_5$: 8.17, 7.63; --.

Column 7, line 49: "7.45" should read -- 7.47 --.

Column 7, line 53: "PYRROLE" should read -- PYRROLO --.

UNITED STATES PATENT AND TRADEMARK OFFICE
CERTIFICATE OF CORRECTION

PATENT NO. : 5,599,812
DATED : February 4, 1997
INVENTOR(S) : S. Rault; J-C Lancelot; H. Prunier; M. Robba; P. Delagrange; P. Renard; G. Adam It is certified that error appears in the above-indentified patent and that said Letters Patent is hereby corrected as shown below:

Column 7, line 54: "QUNIOXALINE" should read -- QUINOXALINE --.

Column 8, lines 34 and 35: "H9" should read -- $H_9$ --; <u>and</u> delete second occurrence "$C_6H_5$; 7.33;". Page 10, Column 8, line 48: "δSH" should read -- δH --.

Column 8, line 49: "H9" should read -- $H_9$ --.

Column 9, line 11: "H9" should read -- $H_9$ --.

Column 9, line 49: "H9" should read -- $H_9$ --.

Column 9, line 51: "$CH_2$: 2.40" should read -- $CH_3$: 2.40 --.

Column 10, line 19: "$OCH_2$: 3.82" should read -- $OCH_3$: 3.82 --.

Column 11, line 4: "H4" should read -- $H_4$ --.

Column 12, line 30: At beginning of the line, "RAZINE[2,3-e]" should read -- RAZINO[2,3-e] --.

UNITED STATES PATENT AND TRADEMARK OFFICE
CERTIFICATE OF CORRECTION

PATENT NO. : 5,599,812
DATED : February 4, 1997
INVENTOR(S) : S. Rault; J-C Lancelot; H. Prunier; M. Robba; P. Delagrange; P. Renard; G. Adam Page 3 of 7

It is certified that error appears in the above-indentified patent and that said Letters Patent is hereby corrected as shown below:

Column 13, line 27: "PY-RROLO" should read -- PYRROLO --.

Column 13, line 33: "PY-RROLO" should read -- PYRROLO --.

Column 13, line 62: Insert -- ] -- at end of the line after "PIPERAZINO".

Column 13, line 63: Delete "]" from beginning of the line.

Column 13, line 67: "LALINE" should read -- XALINE --.

Column 14, line 34: "NOX-ALINE" should read -- NOXALINE --.

Column 14, line 57: "DINO)PYRROL-O-[1,2-a]" should read -- DINO)PYRROLO-[1,2-a] --.

Column 16, line 24: Delete the "-" (dash) at the end of the line and insert -- ) --.

Column 16, line 25: Delete the ")" at the beginning of the line.

Column 16, line 51: Delete the "-" (dash) at the end of the line and insert -- ) --.

Column 16, line 52: Delete the ")" at the beginning of the line.

UNITED STATES PATENT AND TRADEMARK OFFICE
CERTIFICATE OF CORRECTION

PATENT NO. : 5,599,812
DATED : February 4, 1997
INVENTOR(S) : S. Rault; J-C Lancelot; H. Prunier; M. Robba; P. Delagrange; P. Renard; G. Adam It is certified that error appears in the above-indentified patent and that said Letters Patent is hereby corrected as shown below:

Column 19, line 1: "Hg" should read -- $H_9$ --.

Column 19, line 4: "$C_{22}H_{23}N_5O.5HCl$" should read -- $C_{22}H_{23}N_5O.3HCl$ --.

Column 19, line 23: "KBr v cm):" should read -- KBr v $cm^{-1}$): --.

Column 19, line 25: "1H" at beginning of the line should read -- $^1H$ --; and "H9)" at the end of the line should read -- $H_9$) --.

Column 19, line 58: "-3nitropyridine" should read -- -3-nitropyridine --.

Column 22, line 21: Delete "20" at beginning of the line.

Column 23, line 24: "1H" at the beginning of the line should read -- $^1H$ --; and "H9)," should read -- $H_9$), --.

Column 23, line 25: "H2)," at the beginning of the line should read -- $H_2$), --.

Column 23, line 32: "BENZYL)PIPER- AZINO]" should read -- BENZYL)PIPERAZINO] --.

Column 23, line 45: Delete the "v" between "H" and "NMR".

UNITED STATES PATENT AND TRADEMARK OFFICE
CERTIFICATE OF CORRECTION

PATENT NO. : 5,599,812
DATED : February 4, 1997           Page 5 of 7
INVENTOR(S) : S. Rault; J-C Lancelot; H. Prunier;
M. Robba; P. Delagrange; P. Renard;
G. Adam It is certified that error appears in the above-indentified patent and that said Letters Patent is hereby corrected as shown below:

Column 23, line 46:   Delete the ")" between "$H_8$" and "$C_6H_3$),".

Column 24, line 45:   "5-HT1D" should read -- $5\text{-}HT_{1D}$ --.

Column 24, line 56:   "5HT-$_3$" should read -- $5\text{-}HT_3$ --.

Column 24, line 60:   "$^{14}$-CGUANIDINIUM" should read -- $^{14}$C-GUANIDINIUM --.

Column 24, line 63:   "$^{14}$-C-guanidinium" should read -- $^{14}$C-guanidinium --.

Column 25, line 54:   "$^{14}$-C-guanidinium" should read -- $^{14}$C-guanidinium --.

Column 26, line 1:    "$^{14}$-C-guanidinium" should read -- $^{14}$C-guanidinium --.

Column 28, line 57:   "Formula for the preparation of 1000 tablets:" should start a new paragraph.

Column 29, line 28:   "by one more" should read -- by one or more --.

Column 29, line 36:   Insert -- , -- (comma) after the word "radical" and <u>delete</u> the word "to". Page 1 of

UNITED STATES PATENT AND TRADEMARK OFFICE
CERTIFICATE OF CORRECTION

PATENT NO. : 5,599,812
DATED : February 4, 1997
INVENTOR(S) : S. Rault; J-C Lancelot; H. Prunier; M. Robba; P. Delagrange; P. Renard; G. Adam It is certified that error appears in the above-indentified patent and that said Letters Patent is hereby corrected as shown below:

Column 29, line 41: Delete the word "to" before "1 of 2 additional".

Column 29, line 44: "to 4," should read -- or 4, --.

Column 30, line 5: Insert a -- , -- (comma) after "morpholine"; "aminoalkylamines," should read -- aminoalkylamino, --.

Column 30, line 34: "or more of radicals" should read -- or more radicals --.

Column 30, line 44: Insert a -- - -- (dash) between "pharmaceutically" and "acceptable".

Column 30, line 49: Delete the word "from".

Column 30, line 52: Delete the word "from".

UNITED STATES PATENT AND TRADEMARK OFFICE
CERTIFICATE OF CORRECTION

PATENT NO.    : 5,599,812
DATED         : February 4, 1997
INVENTOR(S)   : S. Rault; J-C Lancelot; H. Prunier;
                M. Robba; P. Delagrange; P. Renard;
                G. Adam It is certified that error appears in the above-indentified patent and that said Letters Patent is hereby corrected as shown below:

Column 31, line 3:   Insert a -- - -- (dash) between "pharmaceuticially" and "acceptable". 33.

Column 31, lines 3, 7, 11, 15, 19, and 23:   Delete the "," (comma) after the word "salt"; and change "therefore" to -- thereof --.

Column 32, lines 3, 7 and 11:   Delete the "," (comma) after the word "salt"; change "therefore" to -- thereof --.

Signed and Sealed this

Fifteenth Day of April, 1997

Attest:

BRUCE LEHMAN

*Attesting Officer*                    Commissioner of Patents and Trademarks